(12) United States Patent
Binner et al.

(10) Patent No.: US 11,921,050 B2
(45) Date of Patent: Mar. 5, 2024

(54) PREDICTIVE METHOD USING COLORIMETRIC ANALYSIS OF BODILY FLUIDS

(71) Applicant: Johnson & Johnson Consumer Inc., Skillman, NJ (US)

(72) Inventors: Curt Binner, Furlong, PA (US); Justin Mellinger, Philadelphia, PA (US); Alexandru Paunescu, Clinton, NJ (US)

(73) Assignee: Johnson & Johnson Consumer Inc., Skillman, NJ (US)

( * ) Notice: Subject to any disclaimer, the term of this patent is extended or adjusted under 35 U.S.C. 154(b) by 378 days.

(21) Appl. No.: 17/205,491

(22) Filed: Mar. 18, 2021

(65) Prior Publication Data

US 2021/0293720 A1    Sep. 23, 2021

Related U.S. Application Data

(60) Provisional application No. 62/993,137, filed on Mar. 23, 2020.

(51) Int. Cl.
*G01N 21/78* (2006.01)
*A61F 13/42* (2006.01)
(Continued)

(52) U.S. Cl.
CPC ............. *G01N 21/78* (2013.01); *A61F 13/42* (2013.01); *A61F 13/49* (2013.01);
(Continued)

(58) Field of Classification Search
CPC ........ A61F 13/42; G01N 21/78; G01N 21/31; G01N 33/493; G01N 33/52
See application file for complete search history.

(56) References Cited

U.S. PATENT DOCUMENTS 3,918,433 A    11/1975  Fuisz
4,700,714 A    10/1987  Fuisz
(Continued)

FOREIGN PATENT DOCUMENTS

EP          1779119 B        5/2007
WO    WO 2006/023678 A     3/2006
(Continued)

OTHER PUBLICATIONS

International search report and written opinion dated PCT/US2021/070294.

(Continued)

*Primary Examiner* — Maurice C Smith (57) ABSTRACT

A method for predicting risk of a future disease condition includes the steps of collecting and transporting bodily fluid to at least one colorimetric analyte sensing element, detecting the presence of bodily fluid, collecting optical data relating to the at least one colorimetric analyte sensing element with at least one spectrophotometer after a predetermined time period after detecting the presence of bodily fluid in contact with the colorimetric analyte sensing element, communicating the optical data to a computing system having at least one processor and data storage, analyzing the optical data to determine at least one analyte concentration in the bodily fluid, identifying a threshold analyte concentration of the at least one analyte in the bodily fluid that is an indicator of the risk of developing a future disease condition; and recording the at least one analyte concentration in the bodily fluid over time.

4 Claims, 8 Drawing Sheets

(51) Int. Cl.
*A61F 13/49* (2006.01)
*B01L 3/00* (2006.01)
*C12Q 1/26* (2006.01)
*C12Q 1/28* (2006.01)
*C12Q 1/54* (2006.01)
*G01N 21/31* (2006.01)
*G01N 33/493* (2006.01)
*G01N 33/52* (2006.01)
*G01N 21/77* (2006.01)

(52) U.S. Cl.
CPC ... *B01L 3/502707* (2013.01); *B01L 3/502761* (2013.01); *B01L 3/502776* (2013.01); *C12Q 1/26* (2013.01); *C12Q 1/28* (2013.01); *C12Q 1/54* (2013.01); *G01N 21/31* (2013.01); *G01N 33/493* (2013.01); *G01N 33/52* (2013.01); *B01L 2200/10* (2013.01); *G01N 2021/7756* (2013.01); *G01N 2021/7766* (2013.01); *G01N 2201/062* (2013.01)

(56) References Cited

U.S. PATENT DOCUMENTS

| | | | |
|---|---|---|---|
| 6,203,496 B1 | 3/2001 | Gael et al. | |
| 6,342,037 B1 | 1/2002 | Roe et al. | |
| 8,105,552 B2 | 1/2012 | Xiao et al. | |
| 8,273,939 B2 | 9/2012 | Klofta et al. | |
| 8,293,967 B2 | 10/2012 | Klofta et al. | |
| 9,131,893 B2 | 9/2015 | Faybishenko et al. | |
| 9,820,891 B2 | 11/2017 | Abir | |
| 10,028,701 B2 | 7/2018 | Linton et al. | |
| 10,251,602 B2 | 4/2019 | Faybishenko et al. | |
| 10,285,871 B2 | 5/2019 | Arizti et al. | |
| 10,285,872 B2 | 5/2019 | Arizti et al. | |
| 10,292,112 B2 | 5/2019 | LaVon et al. | |
| 10,383,606 B1 * | 8/2019 | McCord | G01N 33/493 |
| 10,462,750 B2 | 10/2019 | LaVon et al. | |
| 10,492,148 B2 | 11/2019 | LaVon et al. | |
| 10,950,340 B2 | 3/2021 | Ranta et al. | |
| 2004/0220538 A1 | 11/2004 | Panopoulos | |
| 2008/0058740 A1 | 3/2008 | Sullivan et al. | |
| 2008/0266117 A1 | 10/2008 | Song et al. | |
| 2010/0100008 A1 | 4/2010 | Chciuk et al. | |
| 2011/0065593 A1 * | 3/2011 | Labrie | G01N 33/6893 506/13 |
| 2013/0296739 A1 | 11/2013 | Schultz | |
| 2014/0198203 A1 | 7/2014 | Vardi et al. | |
| 2014/0200538 A1 | 7/2014 | Euliano et al. | |
| 2016/0078176 A1 | 3/2016 | Ranta et al. | |
| 2017/0252225 A1 | 9/2017 | Arizti et al. | |
| 2018/0093475 A1 | 4/2018 | Strasemeier et al. | |
| 2018/0149635 A1 | 5/2018 | Abir | |
| 2019/0133524 A1 | 5/2019 | Dong et al. | |
| 2019/0170639 A1 * | 6/2019 | Laude | G01N 21/76 |
| 2020/0206044 A1 | 7/2020 | LaVon et al. | |
| 2020/0222252 A1 | 7/2020 | LaVon et al. | |

FOREIGN PATENT DOCUMENTS

| | | |
|---|---|---|
| WO | WO 2007/073139 A | 6/2007 |
| WO | WO 2017/178417 A | 10/2017 |
| WO | WO 2019/051118 A | 3/2019 |

OTHER PUBLICATIONS

International search report and written opinion dated PCT/US2021/070295.
U.S. Appl. No. 17/447,947, filed Sep. 17, 2021, Johnson & Johnson Consumer Inc.
U.S. Appl. No. 17/205,460, filed Mar. 18, 2021, Binner et al.
U.S. Appl. No. 17/205,473, filed Mar. 18, 2021, Binner et al.
U.S. Appl. No. 17/205,491, filed Mar. 18, 2021, Binner et al.

* cited by examiner

PREDICTIVE METHOD USING COLORIMETRIC ANALYSIS OF BODILY FLUIDS

CROSS-REFERENCE TO RELATED APPLICATIONS

This application claims the benefit of U.S. Provisional application 62/993,137 filed on Mar. 23, 2020, the complete disclosure of which is hereby incorporated herein by reference for all purposes.

BACKGROUND OF THE INVENTION

Field of the Invention

The present invention relates to systems which measure changes in the concentration of analytes in bodily fluids. More particularly, this invention relates to systems which are used to measure the concentration of analytes in urine over time and methods to measure these analytes and detect early onset disease states in the human body.

Description of Related Art

The analytes found in bodily fluids such as urine or sweat potentially carries evidence of developing metabolic system problems. There is a desire for people in and out of the medical establishment to track and analyze changes in the concentration of analytes in bodily fluids over time.

Currently, people and physicians rely on visible symptoms to diagnose systemic metabolic problems. This often prompts physicians to do urine analysis or blood tests to determine presence or concentrations of various analytes in these bodily fluids. So, in today's practice, test such as urine analysis is most often used to confirm symptom-based diagnosis, rather than as initial identification of disease. Some conditions, like diabetic ketoacidosis, show visible symptoms only when a person's condition may already warrant an emergency visit to a physician. Other conditions, like urinary tract infection, may not show visible symptoms and result in renal scarring, which may not manifest itself in health problems until many years later.

Non-invasively measuring the analyte concentration in urine content is also ideally suited for epidemiological studies to rapidly identify problems prevalent in specific geographies. Difficulty of sample collection, however, prevents acceleration of research in this area.

Absorbent articles such as diapers exist with embedded sensors that are only capable of detecting wetness. Often, they transmit that information to a receiving system. The receiving system then alerts a caregiver of a one-time event. These wetness detection systems do not perform a diagnosis.

Some existing diagnostic systems rely on urinalysis strips being dipped into a urine sample and are manually or automatically read by an imaging device or cell phone. Other diagnostic systems rely on urinalysis strips mounted to the exterior surface of an absorbent article, and, once wet, are manually or automatically read by an imaging device or cell phone. In either case, data from present readings can be compared with those of both past and future readings.

In either approach, the reading of the urinalysis strips is performed at a point in time after the strips have become wet with urine. Many of the chemicals used in the test strips are sensitive to time, temperature, degree of wetness, etc. of exposure. So, accurate and repeatable readings are difficult to obtain.

In summary, analytes found in bodily fluid may evidence of developing metabolic system problems. There is a desire for to track and analyze changes in the concentration of analytes in bodily fluids such as urine over time. However, for the data to be valuable, the readings must be accurate and repeatable.

BRIEF SUMMARY OF THE INVENTION

We have developed a novel and useful method for predicting risk of a future disease condition. The method includes the steps of collecting and transporting bodily fluid to at least one colorimetric analyte sensing element, detecting the presence of bodily fluid in contact with the at least one colorimetric analyte sensing element, collecting optical data relating to the at least one colorimetric analyte sensing element with at least one spectrophotometer after a predetermined time period after detecting the presence of bodily fluid in contact with the colorimetric analyte sensing element, communicating the optical data to a computing system having at least one processor and data storage, analyzing the optical data to determine at least one analyte concentration in the bodily fluid, identifying a threshold analyte concentration of the at least one analyte in the bodily fluid that is an indicator of the risk of developing a future disease condition; and recording the at least one analyte concentration in the bodily fluid over time.

DETAILED DESCRIPTION OF THE INVENTION

The present invention relates to systems for use in absorbent articles which measure changes in the concentration of analytes in bodily fluids such as urine over time, and methods for using the system to measure the concentration of analytes in bodily fluids over time, as well as methods to use these analyte measurements over time to detect early onset disease states in the human body.

The presently disclosed subject matter will now be described more fully hereinafter with reference to the accompanying drawings and examples. The presently disclosed subject matter can, however, be embodied in different forms and should not be construed as limited to any specific examples set forth herein and is to be accorded the widest scope consistent with the features described herein. Rather, any specific examples are provided so that this disclosure will be thorough and complete and will fully convey the scope of the invention to those skilled in the art to which the invention belongs. It is believed that one skilled in the art can, based upon the description herein, utilize the present invention to its fullest extent.

Unless otherwise defined, all technical and scientific terms used herein have the same meaning as commonly understood by one of ordinary skill in the art to which this presently described subject matter belongs. All publications, patent applications, patents, and other references mentioned herein are incorporated by reference in their entirety.

The present invention relates to systems and methods to enable monitoring of analyte concentration in an absorbent article. The systems and methods also allow statistical analysis and determination of changes in the health state by the collection of multiple data points over time, which may be evidence of developing metabolic system problems. Other data such as medical and family history as well as current variables such as age, temperature, and/or other current markers may be used to supplement trend and statistical analysis.

Figure 1:
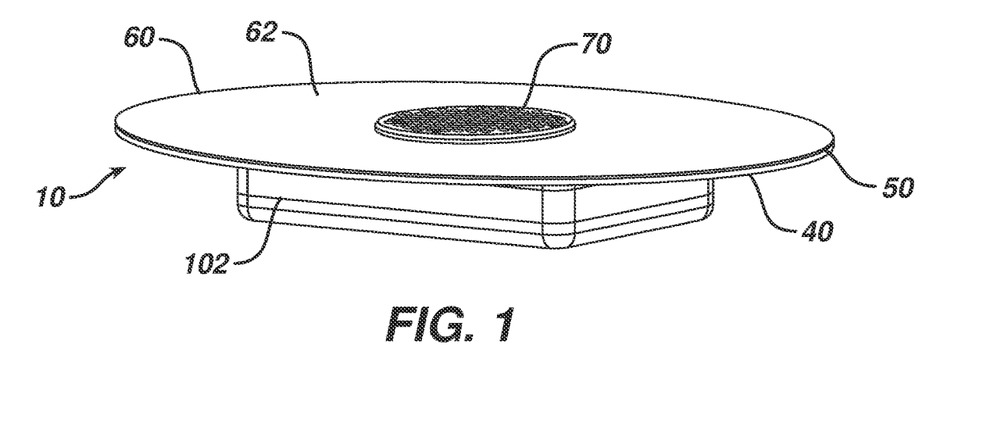
FIG. 1 is a top perspective view of a system for measuring analyte concentration in an absorbent article of the present invention.
Figure 2:
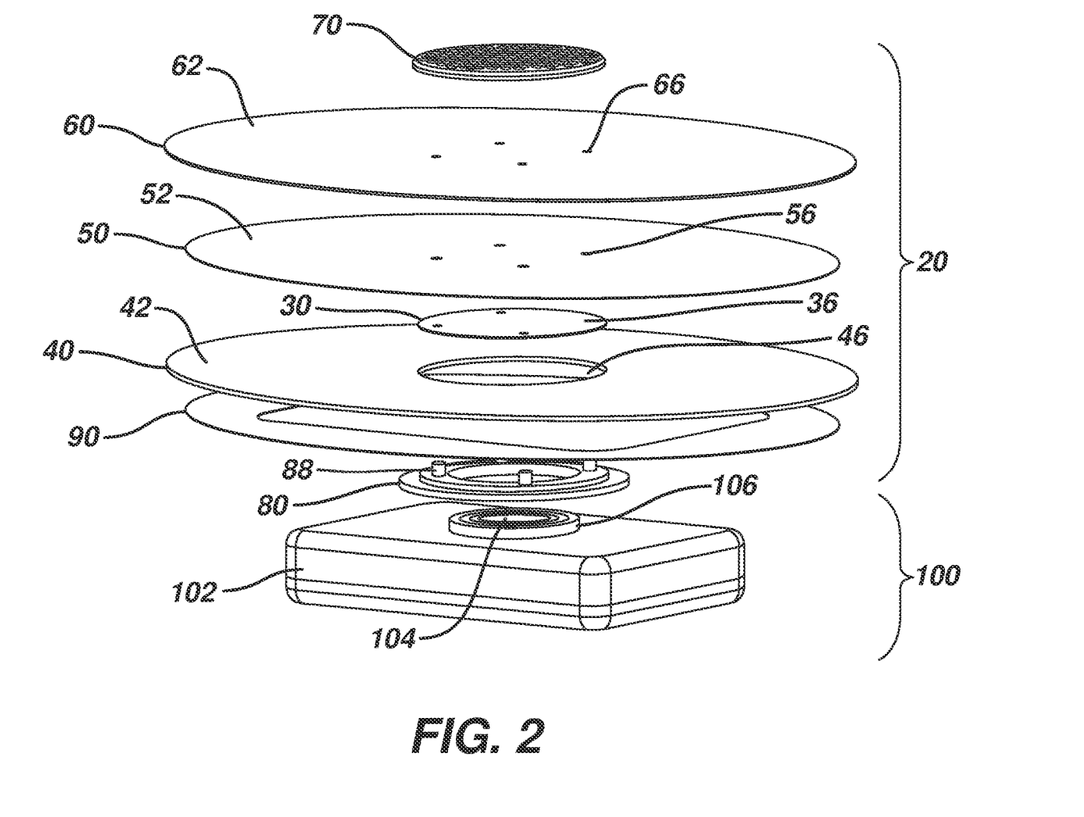
FIG. 2 is an exploded view of the system of FIG. 1.

FIGS. 1 to 6 show an apparatus or system 10 for measuring analyte concentration in an absorbent article. System 10 has an indicator component 20 and a durable component 100. FIG. 1 is a top perspective view of system 10 when full assembled, while FIG. 2 is an exploded view of system 10.

Figure 3:
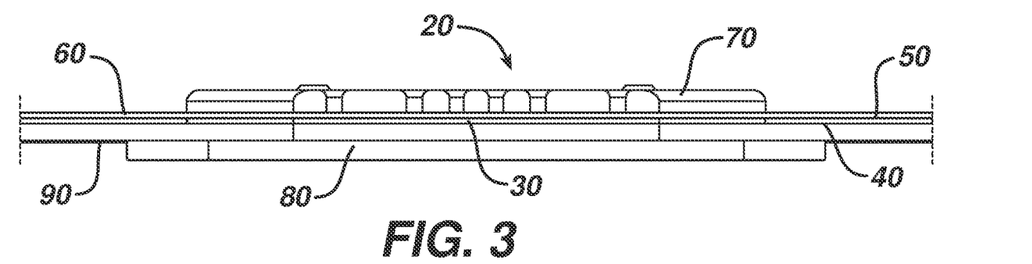
FIG. 3 is a cross-sectional view of the indicator component of the system of FIG. 1.

Indicator component 20 is shown in exploded view in FIG. 2, and in cross-sectional view in FIG. 3. Indicator component 20 includes an indicator zone 21 that has a colorimetric analyte sensing element 30 which may be disposed in an optional second flexible web 40, a fluid transport layer 50, an optional first flexible web 60, an optional top plate 70, a coupler shown here as holding plate 80, and an adhesive layer 90. The indicator component 20 is preferably disposable.

Colorimetric analyte sensing element 30 has perforations 36 and is disposed in aperture 46 of second flexible web 40.

In some embodiments, colorimetric analyte sensing element 30 is a reagent impregnated matrix designed to produce a visual indication of the presence of a preselected analyte in sample produced by the wearer of system 10. Chemistries and methods of detecting analytes by producing a visual indication are well known in the art. In some embodiments, the preselected analyte measured by system 10 may be, glucose, ketone, bilirubin, blood, pH, protein, urobilinogen, nitrite, leukocytes, and/or creatinine, among others.

For example, the absorbent article may be a diaper, the fluid being tested may be urine and the preselected analyte measured by system 10 may be glucose. Glycosuria, or glucose in the urine, is the presence of higher than normal levels of sugar in the urine and may be due to complications with one's kidneys or diabetes. Some of the most common causes of glucose in the urine include: diabetes mellitus, hyperthyroidism, benign glycosuria, liver cirrhosis, or a high sugar diet. In addition, in some embodiments, one of ordinary skill in the art will recognize that choosing appropriate biosensor(s) capable of converting a preferred biomarker into a calorimetrically readable result could be used in genomics, transcriptomics, metabolomics and proteomics as well to determine the presence of inflammatory biomarkers that are present in urine.

As mentioned, colorimetric analyte sensing element 30 is disposed in opening 46 of second flexible web 40 and is in fluid communication with fluid transport layer 50. Fluid transport layer 50, in turn, is in fluid communication with first flexible web 60. Second flexible web 40 has a first side 42, and is made of non-absorbing material, such as a polyethylene foam. Fluid transport layer 50 has a first side 52, and perforations 56, and is made of wicking material, such as fabric or paper, that is effective in spreading and transporting fluid via capillary action. First flexible web 60 has a first side 62, and perforations 66, and is made of a non-absorbing apertured film, such as a polyethylene mesh.

Second flexible web 40, fluid transport layer 50, and first flexible web 60 are designed to aid in the transport of fluid to colorimetric analyte sensing element 30. In use, fluid from the absorbable article first contacts first side 62 of first flexible web 60. Since first flexible web 60 is a non-absorbing apertured film, fluid passes through first flexible web 60 and contacts first side 52 of fluid transport layer 50. The fluid then permeates throughout fluid transport layer 50. The fluid will contact first side 42 of second flexible web 40. But, since second flexible web 40 is made of non-absorbing material, fluid in transport layer 50 does not penetrate second flexible web 40. Finally, the fluid in transport layer 50 comes into contact with colorimetric analyte sensing element 30.

Sensing element 30 disposed in second flexible web 40, fluid transport layer 50, and first flexible web 60 are stacked, as shown in FIGS. 1 to 3, and are held together by top plate 70 and holding plate 80. Holding plate 80 has pins 88. Pins 88 sequentially pass through perforations 36 of colorimetric analyte sensing element 30, perforations 56 of fluid transport layer 50, and perforations 66 of first flexible web 60. Though not shown, top plate 70 has blind holes in which pins 88 are disposed. A friction fit between top plate 70 blind holes and pins 88 hold the components of indicator component 20 together. Alternative assemblies may be held together by other interactions, such as snap fit, ultrasonic weld, heat weld, other mechanical fasteners, and the like.

The top plate and holding plate are arranged and configured to provide a predetermined spacing to accommodate indicator component layers with predetermined fluid transport capacity to the indicator zone. This provides a more controlled delivery of bodily fluid to the indicator zone and the associated timing between the bodily fluid arriving at the indicator zone and the colorimetric measurement, described in more detail, below.

Top plate 70 may have channels on the side facing first side 62 of first flexible web 60. The channel may help direct fluid from the absorbent article to the first side 62 of first flexible web 60.

Figure 4:
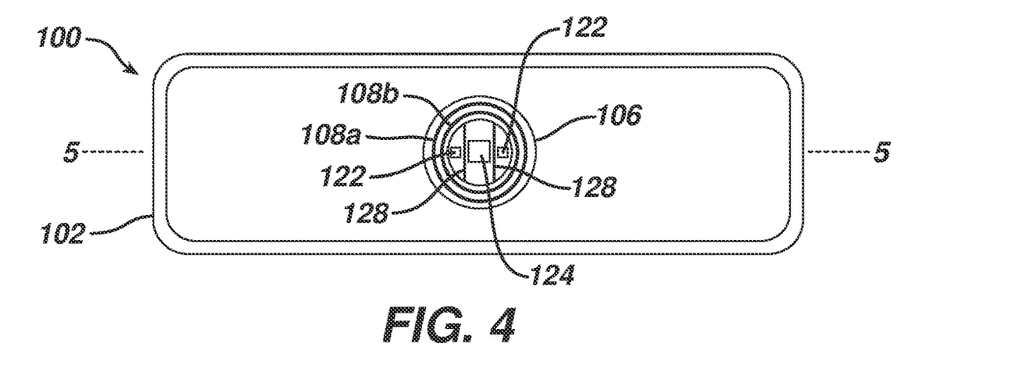
FIG. 4 is a top view of the durable component of the system of FIG. 1.
Figure 5:
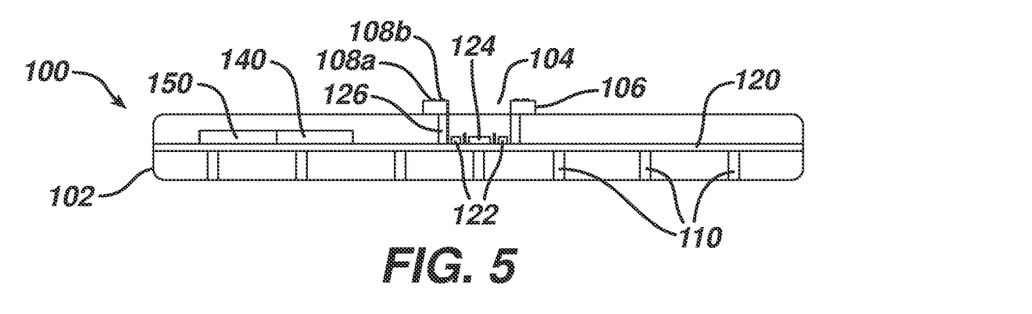
FIG. 5 is a cross-sectional view of the durable component of along the 5-5 plane of FIG. 4.
Figure 6:
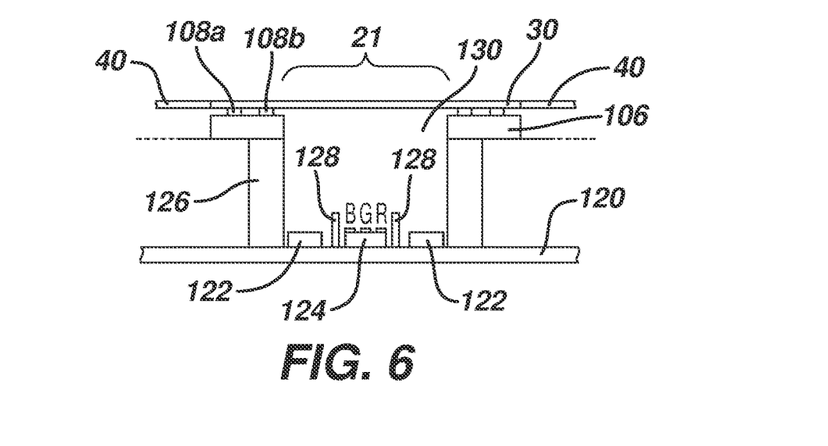
FIG. 6 is a cross-sectional view of the spectrophotometer portion of the durable component of FIG. 5.

Durable component 100 is shown in exploded top perspective view in FIG. 2, in top view in FIG. 4, in cross-sectional view in FIG. 5, and in enlarged cross-sectional view in FIG. 6. Durable component 100 has a housing 102 with a window 104. A spectrophotometer is disposed in housing 102. The components of the spectrophotometer include light sources 122 and photodetector 124. The spectrophotometer is adjacent to and in optical communication with window 104. This allows spectrophotometer to be in optical communication with the colorimetric analyte sensing element 30 of indicator component 20.

As shown in FIG. 2, spectrophotometer includes two light sources 122 and one photodetector 124. If desired, a spectrophotometer may include at least one or more light sources 122 and at least one photodetector 124, for example, at least two or more light sources 122 and at least two or more photodetectors 124.

FIG. 2 also shows male connector protrusion 106 surrounding window 104 on housing 102. Male connector protrusion 106 allows durable component 100 to be releasably attached to indicator component 20.

FIG. 4 is a top view of durable component 100 of system 10. Conductive strips 108a and 108b are disposed on the top surface of male connector protrusion 106, and, as described below, act as a moisture sensor, arranged and configured to communicate the presence of moisture in colorimetric analyte sensing element 30 to the computing system disposed in durable component 100.

FIGS. 4 and 5 also show two light sources 122 and photodetector 124 linearly arranged in system 10 and evenly spaced. Even spacing may be achieved in other ways, such as multiple two light sources 122 evenly disposed in a square or circular arrangement around photodetector 124.

FIGS. 5 and 6 are cross-sectional views of durable component 100. FIG. 5 shows housing 102, window 104, male connector protrusion 106, conductive strips 108a and 108b, and printed circuit board (PCB) 120. FIG. 6 is an enlargement of the region of durable component 100 housing the components of a spectrophotometer.

PCB 120 mechanically supports and electrically connects electronic components using conductive tracks, pads and other features etched from copper sheets laminated onto a non-conductive substrate. Components (e.g. capacitors, resistors, controllers, power sources, light sources, detectors) are generally soldered on PCB 120. PCB 120 has a computing system 140 having one or more processors and a memory, as well as means for electronic communication 150 to send the results of analyses to data processing systems that are external to system 10. Data processing systems that may be used include at least one external device including server computers, client computers, and handheld devices such as cellphones.

FIG. 5 shows PCB 120 supported within the housing 102 of durable component 100 by means of support brackets 110. In other embodiments, PCB 120 may be attached directly to the inner surface of housing 102.

FIG. 6 is an enlargement of the region of durable component 100 housing the components of a spectrophotometer. Light sources 122 and photodetector 124, which are the components of the spectrophotometer, are disposed on the surface of PCB 120. They are shielded from ambient light by shield 126, shown as a cylindrical ring, with the two ends terminating on the surface of PCB 120 and the inner surface of the housing 102 of durable component 100. Skirts 128 are attached to the surface of PCB 120 and serve to optically isolate photodetector 124 from light sources 122. So, in operation, light which emanates from light sources 122 cannot impinge on photodetector 124 without having reflected off of colorimetric analyte sensing element 30.

Alternatively, lenses can be placed over light sources 122 so that in operation light which emanates from light sources 122 cannot impinge on photodetector 124 without having reflected off of colorimetric analyte sensing element 30. Potting materials can also be used to focus the light from light sources 122 at colorimetric analyte sensing element 30.

FIG. 6 also shows light chamber 130. Light chamber 130 is the volume enclosed by the surface of PCB 120, ambient light by shield 126, male connector protrusion 106, conductive strip 108b, and colorimetric analyte sensing element 30. Indicator zone 21 is the area of indicator component 20 where colorimetric analyte sensing element 30 is exposed to light sources 122.

Though two light sources 122 are apparent in FIGS. 5 and 6, durable component 100 may have multiple light sources 122, for example four light sources evenly spaced about the device. Light sources 122 may be light-emitting diodes (LEDs), a semiconductor light source that emits light when current flows through it. LEDs have many advantages over incandescent light sources, including lower energy consumption, longer lifetime, improved physical robustness, smaller size, and faster switching. In the embodiment discussed here, light sources 122 are RGB LEDs. Mixing red, green, and blue sources can produce white light with proper blending of the colors. In addition, the colors emanating from RGB LEDs may be monochromatic, allowing data to be obtained in narrow wavelength regions.

Photodetector 124 is also called a photosensor. Photodetectors are sensors of light or other electromagnetic radiation. A photodetector has a p-n junction that converts light photons into current. The absorbed photons make electron-hole pairs in the depletion region. In some embodiments, photodetector 124 can measure the amount of white light received. In the embodiment discussed here, photodetector 124 specifically measures the red, green, and blue light, allowing data to be obtained in narrow wavelength regions (Note in FIG. 6 the "R", "G" and "B" above photodetector 124).

In system 10 for measuring analyte concentration in an absorbent article, light sources 122 emit light in narrow red, green, and blue wavelengths. The emitted light waves reflect off of colorimetric analyte sensing element 30. The reflected light is then measure by photodetector 124. In this embodiment, sources 122 sequentially emit red light, green light, and blue light, allowing for the near simultaneous collection of three data points. In other embodiments, the sequence of emitted red light, green light, and blue light may vary.

The components of the spectrophotometer may be coated with a protective material. The protective material keeps the moisture from the colorimetric analyte sensing element 30 from contacting, and potentially damaging, the components of the spectrophotometer.

Indicator component 20 is arranged and configured for releasable attachment to the durable component 100. When assembled, colorimetric analyte sensing element 30 is disposed adjacent to and in optical communication with window 104 and the elements of the spectrophotometer.

FIGS. 4 to 6 also show conductive strips 108a and 108b that are disposed on the top surface of male connector protrusion 106. Conductive strips 108a and 108b act as a moisture sensor in system 10 and are arranged and configured to communicate the presence of moisture in colorimetric analyte sensing element 30 to the computing system disposed in durable component 100. In turn, the computing system disposed in durable component 100 is operatively connected to the moisture sensor and the components of the spectrophotometer.

As shown in FIG. 6, conductive strips 108a and 108b are adjacent to colorimetric analyte sensing element 30. When moisture impinges on colorimetric analyte sensing element 30, it will also contact portions of conductive strips 108a and 108b.

Figure 7:
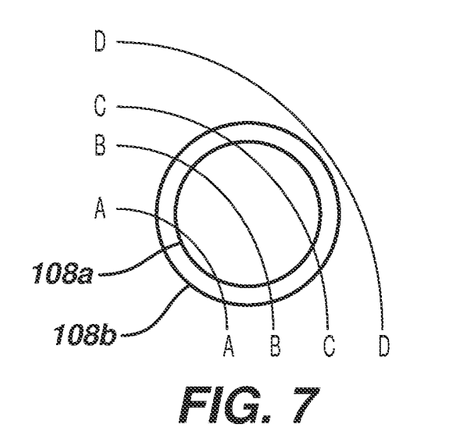
FIG. 7 is a top view of the moisture sensor element of the indicator component of the system for measuring analyte concentration in an absorbent article as a moisture front crosses the element.

FIGS. 7 and 8 describe the function of conductive strips 108a and 108b in the moisture sensor in system 10. FIG. 7 is a top view of conductive strips 108a and 108b at several time points during the progression of a moisture front across the strips. The progression of the front is shown as A-A, B-B, C-C and D-D. At time point A-A, the moisture front has progressed partially across conductive strips 108a and 108b. Further progression across strips 108a and 108b are shown as time points B-B and C-C, while D-D shows a time point where the moisture front has fully crossed strips 108a and 108b.

Figure 8:
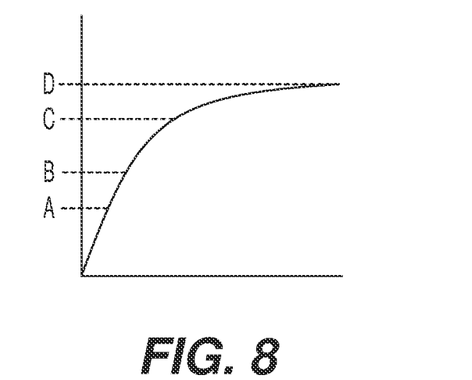
FIG. 8 is a capacitance versus time plot as a moisture front crosses the moisture sensor element of the indicator component of the system for measuring analyte concentration.

FIG. 8 shows an example of the change in an electrical property between strips 108a and 108b as the moisture front progresses across the strips. In this embodiment, FIG. 8 shows a capacitance versus time plot as a moisture front crosses strips 108a and 108b. Line A on FIG. 8 corresponds to time point A-A, where the moisture front has progressed partially across conductive strips 108a and 108b. Capacitance is shown to increase to line B and then line C as time points B-B and C-C show further progression across strips 108a and 108b. Finally, line D, where capacitance is shown to level of corresponds to time point D-D, where the moisture front has fully crossed strips 108a and 108b. At point D-D, colorimetric analyte sensing element 30 has been fully saturated with moisture.

Though capacitance is discussed in this embodiment, other electrical properties, such as resistance, will also change as the moisture front progresses across strips 108a and 108b.

The moisture sensing system described above allows the spectrophotometer to perform its reading of the emitted light waves reflect off of colorimetric analyte sensing element 30 at a point in time after the strips have become wet with moisture. This solves the issue of chemicals used in the test strips are sensitive to time, temperature, and degree of wetness, allowing accurate and repeatable readings are to be obtained.

In a preferred embodiment, the plurality of light sources 122 are four narrow beam LEDs spaced about the photodetector 124. Therefore, the onset of wetness can be detected by a change of impedance by conductive strips 108a and 108b. The accuracy of the beginning of sufficient saturation of the colorimetric analyte sensing element 30 can be improved by sequentially activating each of the narrow beam LEDs and comparing the light detected by photodetector 124. If there is a significant difference among the data returned by the photodetector 124 as a result of different narrow beam LEDs, the colorimetric analyte sensing element 30 may not be sufficiently saturated for reliable analysis. Therefore, in this embodiment, the system may begin collecting optical data relating to the colorimetric analyte sensing element 30 after a predetermined time period following bodily fluid contact with the colorimetric analyte sensing element 30 as determined by (1) a change of impedance by conductive strips 108a and 108b and (2) relatively consistent data returned by the photodetector 124 as a result of different narrow beam LEDs indicating substantially uniform wetness of the colorimetric analyte sensing element 30.

Although the embodiment described above is an embodiment of a system 10 for measuring analyte concentration in an absorbent article which has an indicator component 20 and a durable component 100, it is envisioned that in some cases durable component 100 can be combined with a plurality of indicator components 20 to create a kit for measuring analyte concentration in an absorbent article. The kit has at least one, preferably one or more, individually packaged indicator components 20. This allows for the kit to measure analyte concentration in an absorbent article daily, or weekly, or monthly, or one or more times a day, or week or month. When used in this manner, system 10 is used to track changes in measured analyte concentration over the course of days, week, months, or even years.

Disposable absorbent articles for use in system 10 for measuring analyte concentrations include absorbent hygiene articles such as diapers (including infant diapers, training pants and adult incontinence products) and pads (including feminine sanitary napkins and pantiliners and nursing pads).

For example, an absorbent article for use in system 10 for measuring analyte concentrations is a diaper, and analyte concentrations are being measured in urine. Indicator component 20 has attachment means such as an adhesive layer 90. Adhesive layer 90 is used to attach, or couple, indicator component 20 of system 10 to the fluid transport layer of the diaper. System 10 may be attached to a body-facing surface of the diaper. Other attachment means will be readily apparent, including without limitation, mechanical fasteners, such as clips, clamps, hook-and-loop systems, and bands; magnetic (including static electricity); friction; and the like. Indicator component may be arranged and configured for releasable attachment to a diaper.

Figure 9:
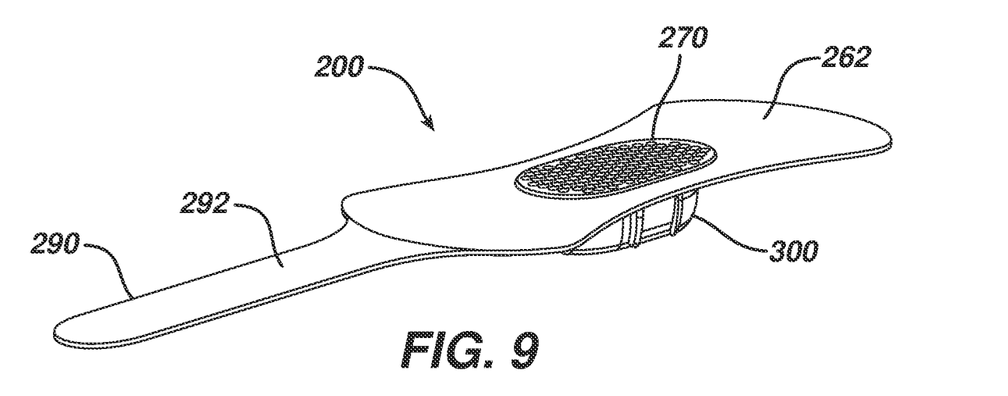
FIG. 9 is a top perspective view of a system for measuring analyte concentration of the present invention.
Figure 10:
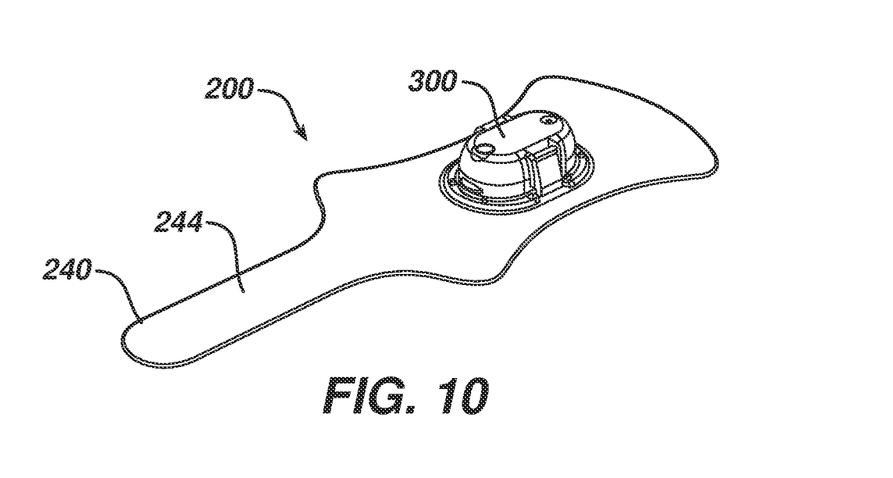
FIG. 10 is a bottom perspective view of the system for measuring analyte concentration of FIG. 9.

The system for measuring analyte concentration in an absorbent article may have a plurality of colorimetric analyte sensing elements. FIGS. 9 to 17 show a system for measuring analyte concentration in an absorbent article of the present invention. System 200 has an indicator component 220 and a durable component 300. FIGS. 9 and 10 are top and bottom, respectively, of system 200 when full assembled.

Figure 11:
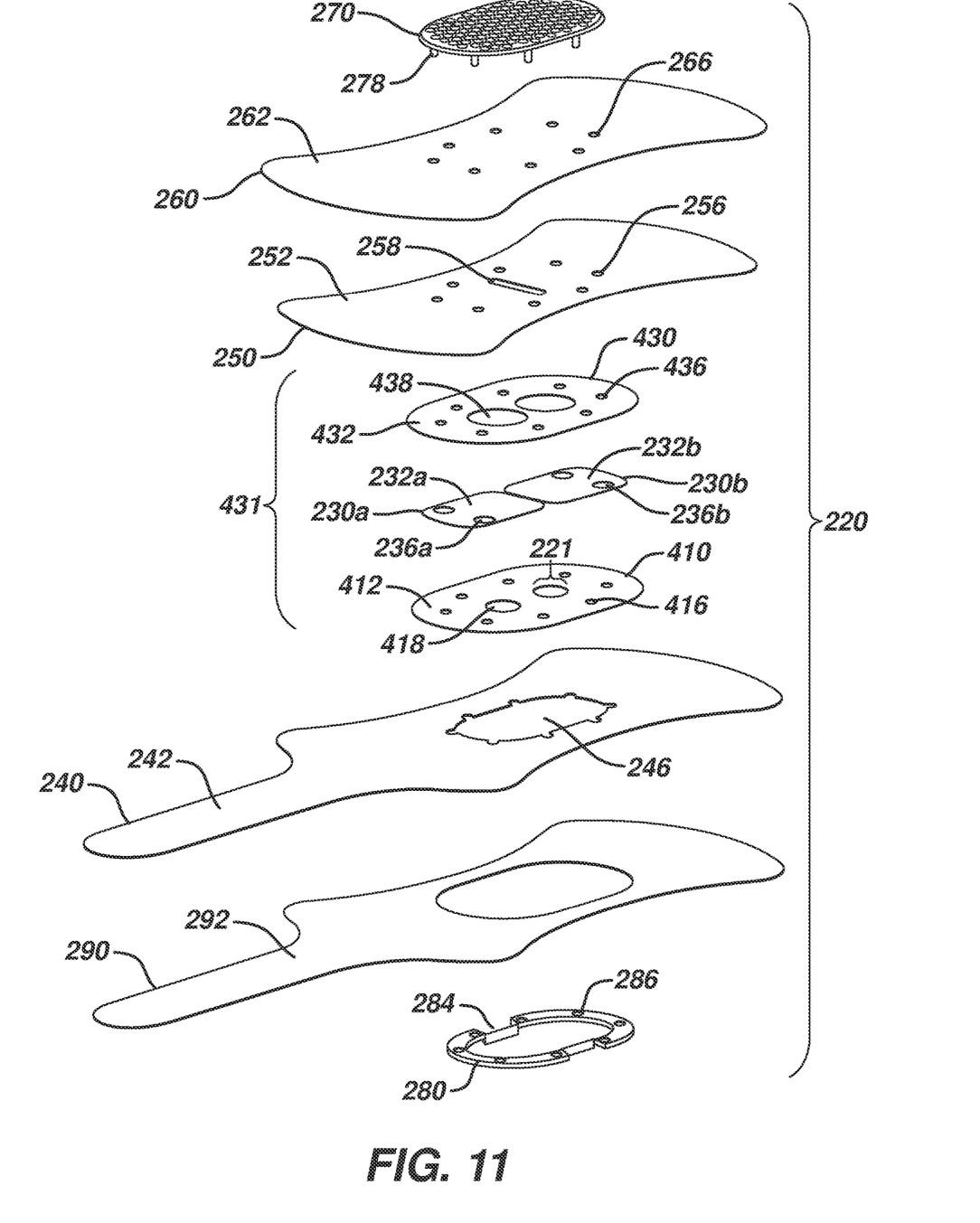
FIG. 11 is an exploded view of the indicator component of the system of FIGS. 9 and 10.

Indicator component 220 is shown in exploded view in FIG. 11. Indicator component 220 includes an indicator zone 221 that has a pair of colorimetric analyte sensing elements, first colorimetric analyte sensing element 230a, and second colorimetric analyte sensing element 230b. First colorimetric analyte sensing element 230a has a first side 232a and a second side 234a, as well as perforations 236a. Second colorimetric analyte sensing element 230b has a first side 232b and a second side 234b, as well as perforations 236b.

Colorimetric analyte sensing elements 230a, 230b may be reagent impregnated matrices designed to produce a visual indication of the presence of a preselected analyte in sample produced by the wearer of system 200. Chemistries and methods of detecting analytes by producing a visual indication are well known in the art. The preselected analyte measured by system 200 may be, glucose, ketones, bilirubin, blood, pH, protein, urobilinogen, nitrite, leukocytes, and/or creatinine, among others.

Colorimetric analyte sensing elements 230a, 230b may be designed to produce a visual indication of the presence of the same preselected analyte in sample produced by the wearer of system 200. In this case, colorimetric analyte sensing elements 230a, 230b act to confirm the analysis. Colorimetric analyte sensing elements 230a, 230b may also be designed to produce a visual indication of the presence of different preselected analytes in sample produced by the wearer of system 200.

Again, the absorbent article may be a diaper, the fluid being tested is urine and the preselected analyte measured by system 200 is glucose. Glycosuria, or glucose in the urine, is the presence of higher than normal levels of sugar in the urine and may be due to complications with one's kidneys or diabetes.

The preselected analytes measured by system 200 may also be ketones. If cells in the body do not get sufficient glucose, the body burns fat for energy instead. This produces ketones which can show up in the blood and urine. High ketone levels in urine may indicate diabetic ketoacidosis (DKA), a complication that can lead to a coma or even death.

Some of the most common causes of glucose or ketones in the urine include: diabetes mellitus, hyperthyroidism, benign glycosuria, liver cirrhosis, or a high sugar diet. In addition, in some embodiments, one of ordinary skill in the art will recognize that choosing appropriate biosensor(s) capable of converting a preferred biomarker into a calorimetrically readable result could be used in genomics, transcriptomics, metabolomics and proteomics as well to determine the presence of inflammatory biomarkers that are present in urine.

The other components of indicator component 220 include an optional top plate 270, an optional first flexible web 260, a fluid transport layer 250, a second flexible web 240, an adhesive layer 290, and a coupler shown here as holding plate 280.

Colorimetric analyte sensing elements 230a, 230b are encapsulated between first encapsulation layer 410 and second encapsulation layer 430 to form a fluid impervious envelope 431. First encapsulation layer 410 has a first side 412 and a second side 414, as well as perforations 416 and apertures 418. Second encapsulation layer 430 has a first side 432 and a second side 434, as well as perforations 436 and apertures 438.

Figure 12:
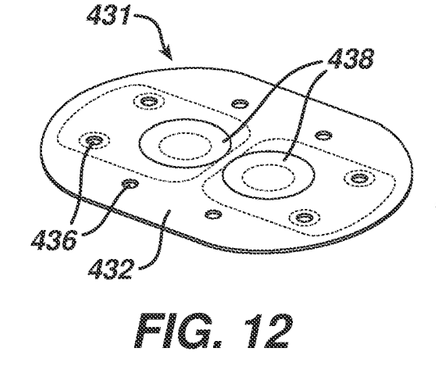
FIG. 12 is a top perspective view of the fluid impervious envelope encapsulating colorimetric analyte sensing elements of the indicator component of FIG. 11.
Figure 13:
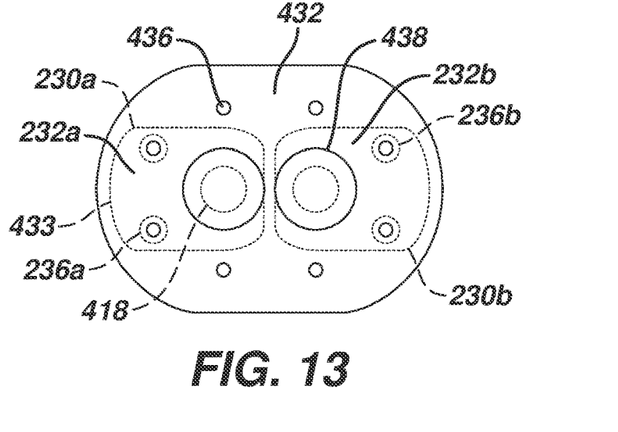
FIG. 13 is a top view of the fluid impervious envelope encapsulating colorimetric analyte sensing elements of the indicator component FIG. 11.

FIG. 12 is a top perspective view of the fluid impervious envelope 431 encapsulating colorimetric analyte sensing elements 230a, 230b of indicator component 220 of system 200. FIG. 13 shows a top view of the fluid impervious envelope 431 encapsulating colorimetric analyte sensing elements of FIG. 12. The figures show, in solid lines, first side 432, perforations 436 and aperture 438 of second encapsulation layer 430. In dashed lines, the figures show colorimetric analyte sensing elements 230a, 230b, their first sides 232a, 232b and perforations 236a, 236b as well as apertures 418 of first encapsulation layer 410. The dashed lines showing colorimetric analyte sensing elements 230a, 230b, also outline discrete pockets 433 (one of two shown in FIG. 13) formed when first encapsulation layer 410 and second encapsulation layer 430 are sealed together where their surfaces contact.

When assembled, first perforations 436 of second encapsulation layer 430 are in alignment with perforations 236a, 236b of colorimetric analyte sensing elements 230a, 230b, as well as perforations 416 of first encapsulation layer 410 (not shown). In addition, apertures 438 of second encapsulation layer 430 are in alignment with apertures 418 of first encapsulation layer 410.

Figure 14:
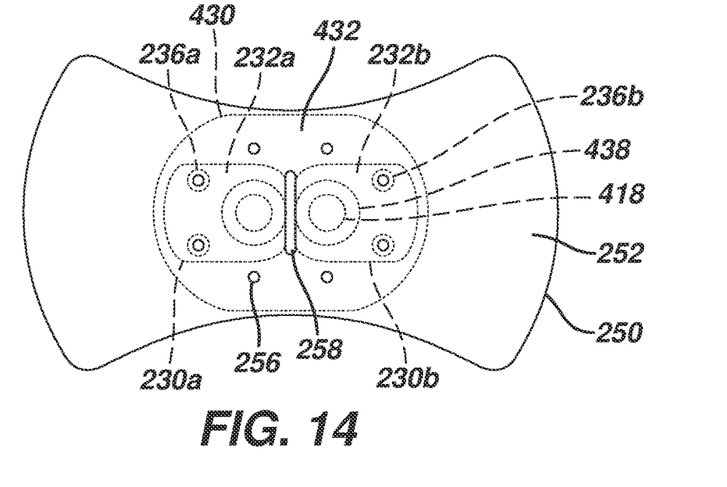
FIG. 14 is a top view of partially assembled indicator component of FIG. 11.

The fluid impervious envelope 431 encapsulating colorimetric analyte sensing elements 230a, 230b of indicator component 220 of system 200 is disposed on fluid transport layer 250. This partially assembled indicator component of the system 200 is shown in a top in view FIG. 14, and in bottom view in FIG. 15. FIG. 14 shows, in solid lines, first side 252, first perforations 256 and second perforation 258 of fluid transport layer 250. In dashed lines, the figures show colorimetric analyte sensing elements 230a, 230b, their first sides 232a, 232b and perforations 236a, 236b, as well as apertures 418 of first encapsulation layer 410 and first side 432 and apertures 438 of second encapsulation layer 430.

Figure 15:
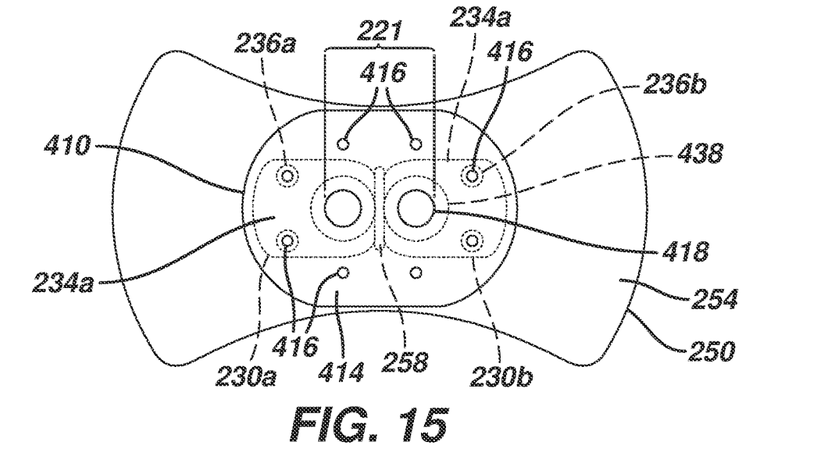
FIG. 15 is a bottom view of partially assembled indicator component of the FIG. 11.

FIG. 15 shows, in solid lines, second side 252 of fluid transport layer 250, as well as second side 414, perforations 416 and apertures 418 of first encapsulation layer 410. In dashed lines, the figures show colorimetric analyte sensing elements 230a, 230b, their second sides 234a, 234b and perforations 236a, 236b, and second perforation 258 of fluid transport layer 250.

Second flexible web 240 has a first side 242, a second side 244 and opening 246, and is made of non-absorbing material, such as a polyethylene foam. The fluid impervious envelope 431 encapsulating colorimetric analyte sensing elements 230a, 230b is disposed on second flexible web 240, specifically in opening 246 of second flexible web 240 and is in fluid communication with fluid transport layer 250. Fluid transport layer 250, in turn, is in fluid communication with first flexible web 260. First flexible web 260 has a first side 262, and perforations 266, and is made of a non-absorbing apertured film, such as a polyethylene mesh.

Second flexible web 240, fluid transport layer 250, and first flexible web 260 are designed to control the transport of bodily fluids to the colorimetric analyte sensing elements 230a, 230b and to limit cross-contamination of fluids among different colorimetric analyte sensing elements. In use, fluid from the absorbable article first contacts first side 262 of first flexible web 260. Since first flexible web 260 is a non-absorbing apertured film, fluid passes through first flexible web 260 and contacts first side 252 of fluid transport layer 250. The fluid then permeates throughout fluid transport layer 250. The fluid will contact first side 242 of second flexible web 240. But, since second flexible web 240 is made of non-absorbing material, fluid in transport layer 250 does not penetrate second flexible web 240. Finally, the fluid in transport layer 250 passes through apertures 438 of second encapsulation layer 430 to contact the colorimetric analyte sensing elements 230a, 230b. Cross-contamination between the two colorimetric analyte sensing elements is eliminated or at least made insignificant and not detectable by means of the fluid barrier defined by the gap in capillarity within the fluid transport layer 250 provided by the second perforation 258.

Sensing elements 230a, 230b, first encapsulation layer 410, second encapsulation layer 430, second flexible web 240, fluid transport layer 250, and first flexible web 260 are stacked, as shown in FIG. 11, and are held together by top plate 270 and holding plate 280. Top plate 270 has pins 278. Pins 278 sequentially pass through perforations 266 of first flexible web 260, perforations 256 of fluid transport layer 250, perforations 416 of first encapsulation layer 410, perforations 236a, 236b of colorimetric analyte sensing elements 230a, 230b, first perforations 436 of second encapsulation layer 430, opening 246 of second flexible web 240, and are finally disposed in blind holes 286 of holding plate 280. A friction fit between top plate pins 278 and blind holes 286 hold the components of indicator component 220 together. Alternative assemblies may be held together by other interactions, such as snap fit, ultrasonic weld, heat weld, other mechanical fasteners, and the like.

Top plate 270 may have one or more channels on the side facing first side 262 of first flexible web 260. The channel(s) may help direct fluid from the absorbent article to the first side 262 of first flexible web 260.

Indicator component 220 may have attachment means, such as adhesive layer 290. Adhesive layer 290 has a first side 292, and is used to attach, or couple, indicator component 220 of system 200 to the fluid transport layer of the absorbent article, such as a diaper.

Figure 16:
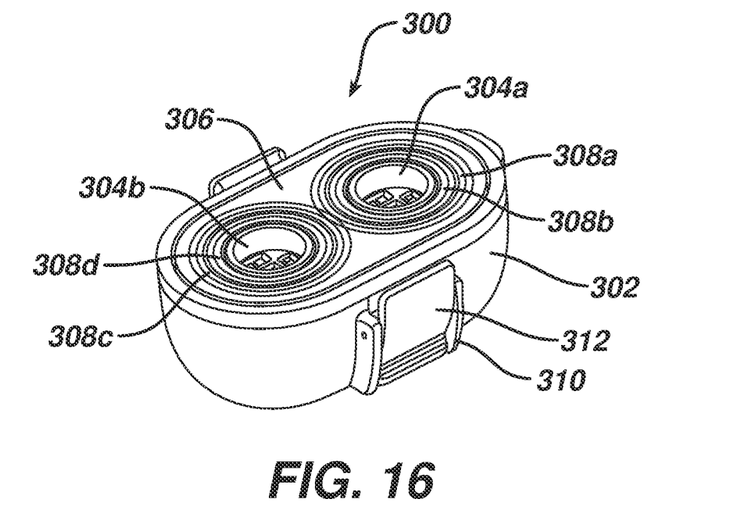
FIG. 16 is a top perspective view the durable component of the system of FIGS. 9 and 10.
Figure 17:
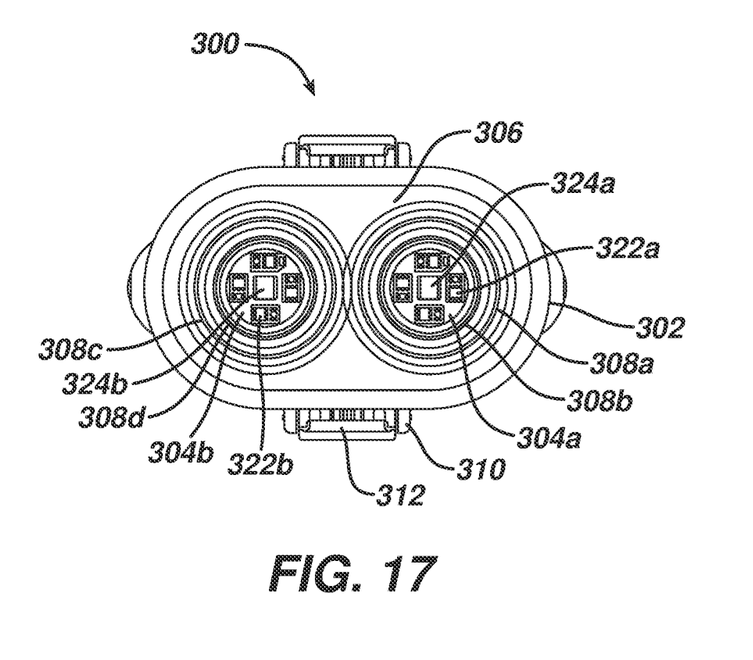
FIG. 17 is a top view of the durable component of the system of FIGS. 9 and 10.

A durable component 300 of the system is shown in top perspective view in FIG. 16, and in top view in FIG. 17. Durable component 300 has a housing 302 with a pair of windows, first window 304a, and second window 304b. Durable component 300 also has a flat top surface 306. A pair of spectrophotometers are disposed in housing 302. The first spectrophotometer is adjacent to and in optical communication with first window 304a. The components of the first spectrophotometer include light sources 322a and photodetector 324a. First spectrophotometer is in optical communication with colorimetric analyte sensing element 230a. The second spectrophotometer is adjacent to and in optical communication with second window 304b. The components of the second spectrophotometer include light sources 322b and photodetector 324b. Second spectrophotometer is in optical communication with colorimetric analyte sensing element 230b. While the durable component 300 has been shown with two spectrophotometers, additional spectrophotometers may be included for measurements of additional analytes or bodily fluid conditions, such as pH, temperature, etc. Indicator zone 221 is the area of indicator component 220 where colorimetric analyte sensing element 230a is exposed to light sources 322a.

Thought not shown, durable component 300 also has a printed circuit board (PCB) with a computing system having one or more processors and a memory, as well as means for electronic communication to send the results of analyses to data processing systems that are external to system 200. Data processing systems that may be used include at least one external device including server computers, client computers, and handheld devices such as cellphones.

As shown in FIGS. 16 and 17, the first and second spectrophotometer may include four light sources 322a, 322b and each spectrophotometer has one photodetector 324a, 324b. Each spectrophotometer may have associated therewith at least one light sources 322a, 322b. Each spectrophotometer may include at least six or more light sources 322a, 322b. As mentioned earlier, light sources 322a, 322b may be light-emitting diodes (LEDs), and more specifically, RGB LEDs. Light sources 322a, 322b may sequentially emit red light, green light, and blue light, allowing for the near simultaneous collection of three data points, or, the sequence of emitted red light, green light, and blue light may vary.

The photodetectors in the spectrometers 324a, 324b, as discussed previously, may specifically measure the red, green, and blue light, allowing data to be obtained in narrow wavelength regions. The light waves emitted from light sources 322a reflect off of colorimetric analyte sensing element 230a, and the reflected light is measure by photodetector 324a. The light waves emitted from light sources 322b reflect off of colorimetric analyte sensing element 230b, and the reflected light is measure by photodetector 324b. The components of the spectrophotometer may be coated with a protective material. The protective material keeps the moisture from the colorimetric analyte sensing elements 230a, 230b from contacting, and potentially damaging, the components of the spectrophotometers.

FIGS. 16 and 17 also show connectors 310 disposed on housing 302. Connectors 310 comprise a standard spring-loaded clips 312 that are biased to hold clips 312 to housing 302 of durable component 300. As shown in FIG. 11, holding plate 280 has receiving elements 286 disposed thereon. To releasably attach durable component 300 to holding plate 280, clips 312 are fastened to receiving elements 286. By this means, durable component 300 is releasably attach to indicator component 220. Other attachment means will be readily apparent, including without limitation, mechanical fasteners, such as clamps, hook-and-loop systems, threaded apertures, bayonet couplings, straps, belts, and bands; magnetic (including static electricity); friction; and the like.

FIG. 17 also shows conductive strips 308a, 308b, 308c and 308d disposed on top surface 306 of durable component 300. Conductive strips 308a, 308b, 308c and 308d act as moisture sensors, arranged and configured to communicate the presence of moisture in colorimetric analyte sensing elements 230a, 230b to the computing system disposed in durable component 300. As shown in FIG. 17, conductive strips 308a and 308b are associated with first window 304a and colorimetric analyte sensing element 230a. Conductive strips 308c and 308d are associated with second window 304b and colorimetric analyte sensing element 230b. The computing system disposed in durable component 300 is operatively connected to the moisture sensors as well as the components of the spectrophotometer.

Conductive strips 308a and 308b are adjacent to colorimetric analyte sensing element 230a. When moisture impinges on colorimetric analyte sensing element 230a, it will also contact portions of conductive strips 308a and 308b. Conductive strips 308c and 308d are adjacent to colorimetric analyte sensing element 230b. When moisture impinges on colorimetric analyte sensing element 230b, it will also contact portions of conductive strips 308c and 308d.

Figure 18:
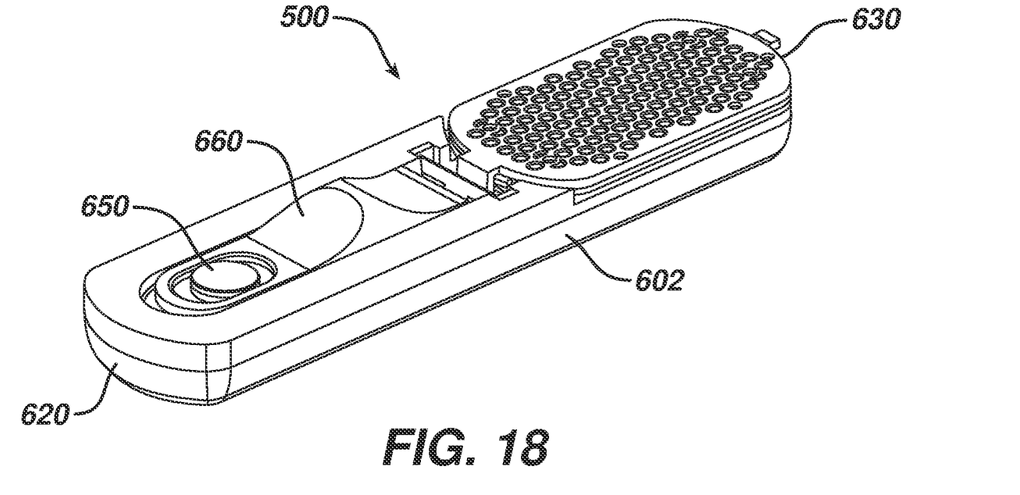
FIG. 18 is a top perspective view of a system for measuring analyte concentration in a bodily fluid of the present invention.
Figure 19:
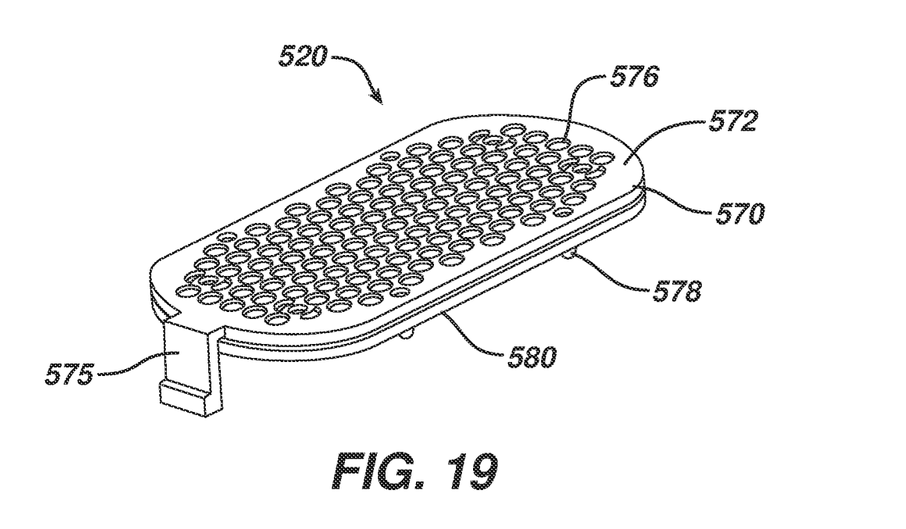
FIG. 19 is a top perspective view of the indicator component of the system of FIG. 18.
Figure 20:
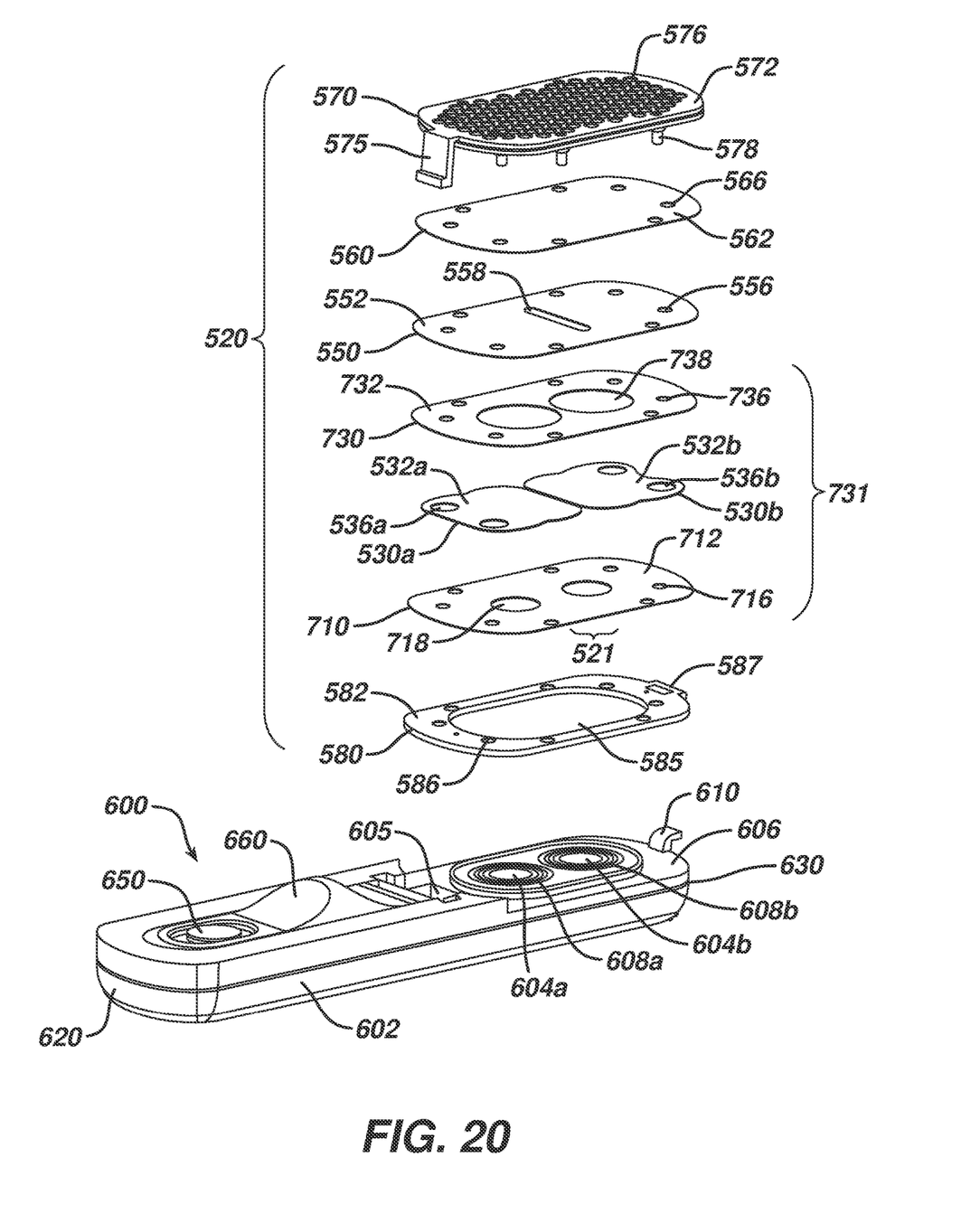
FIG. 20 is a partially exploded view of the system of FIG. 18.

The mode of operation of conductive strips 308a, 308b, 308c and 308d as moisture sensors are identical to the operation of conductive strips 108a and 108b as described in FIGS. 7 and 8. The moisture front progresses partially, and finally, fully across conductive strips 308a and 308b, and 308c and 308d. The system for measuring analyte concentrations in bodily fluids may be used in an absorbent article, or it may be directly contacted by bodily fluids outside of an absorbent article. For example, the system can contact bodily fluids collected in a specimen container or may come into contact with bodily fluids such as urine as the fluid is expelled from the human body. FIGS. 18 to 20 show a system for measuring analyte concentration in a bodily fluid of the present invention. System 500 has an indicator component 520 and a durable component 600. FIG. 18 is a top perspective view of system 500 when full assembled. FIG. 19 is a top perspective view of the indicator component 520 of system 500. FIG. 20 is a partially exploded view of system 500, where indicator component 520 is shown in exploded view.

In FIG. 20, indicator component 520 includes an indicator zone 521 is shown to have a pair of colorimetric analyte sensing elements, first colorimetric analyte sensing element 530a, and second colorimetric analyte sensing element 530b. First colorimetric analyte sensing element 530a has a first side 532a and perforations 536a. Second colorimetric analyte sensing element 530b has a first side 532b and perforations 536b.

As discussed before, colorimetric analyte sensing elements 530a, 530b may be reagent impregnated matrices designed to produce a visual indication of the presence of a preselected analyte in sample produced by the user of system 500. The preselected analyte measured by system 500 may be, glucose, ketones, bilirubin, blood, pH, protein, urobilinogen, nitrite, leukocytes, and/or creatinine, among others.

Again, colorimetric analyte sensing elements 530a, 530b may be designed to indicate the presence of the same preselected analyte in sample produced by the user of system 500. In this case, colorimetric analyte sensing elements 530a, 530b act to confirm the analysis. Colorimetric analyte sensing elements 530a, 530b may also be designed to produce a visual indication of the presence of different preselected analytes in sample produced by the user of system 500.

Again, the fluid being tested may be urine and the preselected analyte measured by system 500 is glucose, one or more ketones, or combinations thereof. The presence of higher than normal levels of glucose and/or ketones in the urine and may be due to complications with the user's kidneys, or other conditions such as diabetes mellitus, hyperthyroidism, benign glycosuria, liver cirrhosis, or a high sugar diet.

In addition, choosing appropriate biosensor(s) capable of converting a preferred biomarker into a calorimetrically readable result may be used in genomics, transcriptomics, metabolomics, and proteomics as well to determine the presence of inflammatory biomarkers that are present in urine or other bodily fluids.

The other components of indicator component 520 include a top plate 570, a first flexible web 560, a fluid transport layer 550, a first encapsulation layer 710, a second encapsulation layer 730, and a coupler shown here as holding plate 580.

Colorimetric analyte sensing elements 530a, 530b are encapsulated between first encapsulation layer 710 and second encapsulation layer 730 to form a fluid impervious envelope 731. First encapsulation layer 710 has a first side 712, perforations 716, and apertures 718. Second encapsulation layer 730 has a first side 732, perforations 736, and apertures 738.

When assembled in indicator component 520, perforations 716 of first encapsulation layer 710 are in alignment with perforations 536a, 536b of colorimetric analyte sensing elements 530a, 530b, as well as perforations 736 of second encapsulation layer 730. In addition, apertures 718 of first encapsulation layer 710 are in alignment with apertures 738 of second encapsulation layer 730.

FIG. 20 also shows fluid transport layer 550 and first flexible web 560. When assembled in indicator component 520, fluid transport layer 550 is disposed on encapsulated colorimetric analyte sensing elements 530a, 530b of indicator component 520 of system 500. Fluid transport layer 550 has first side 552, first perforations 556 and second perforation 558. First flexible web 560 is disposed on fluid transport layer 550, and has a first side 562, and perforations 566, and is made of a non-absorbing apertured film, such as a polyethylene mesh.

When assembled in indicator component 520, colorimetric analyte sensing elements 230a, 230b, which are encapsulated in the fluid impervious envelope 731, are in fluid communication with fluid transport layer 550. Fluid transport layer 550, in turn, is in fluid communication with first flexible web 560.

Fluid transport layer 550 and first flexible web 560 are designed to control the transport of bodily fluids to the colorimetric analyte sensing elements 530a, 530b and to limit cross-contamination of fluids among different colorimetric analyte sensing elements. In use, bodily fluid first contacts first side 562 of first flexible web 560. Since first flexible web 560 is a non-absorbing apertured film, fluid passes through first flexible web 560 and contacts first side 552 of fluid transport layer 550. The fluid then permeates throughout fluid transport layer 550. Finally, the fluid in transport layer 550 passes through apertures 738 of second encapsulation layer 730 to contact the colorimetric analyte sensing elements 530a, 530b. Again, cross-contamination between the two colorimetric analyte sensing elements is eliminated or at least made insignificant and not detectable by means of the fluid barrier defined by the gap in capillarity within the fluid transport layer 550 provided by the second perforation 558.

Sensing elements 530a, 530b, first encapsulation layer 710, second encapsulation layer 730, fluid transport layer 550, and first flexible web 560 are stacked, as shown in FIG. 20, and are held together by top plate 570 and holding plate 580. Top plate 570 has pins 578. Pins 578 sequentially pass through perforations 566 of first flexible web 560, perforations 556 of fluid transport layer 550, perforations 716 of first encapsulation layer 710, perforations 536a, 536b of colorimetric analyte sensing elements 530a, 530b, perforations 736 of second encapsulation layer 730, and are finally disposed in blind holes 586 on first side 582 of holding plate 580. A friction fit between top plate pins 578 and blind holes 586 hold the components of indicator component 520 together. Alternative assemblies may be held together by other interactions, such as snap fit, ultrasonic weld, heat weld, other mechanical fasteners, and the like.

Top plate 570 has apertures 576 which help direct fluid to first side 562 of first flexible web 560. Top plate 570 also has disposed thereon protrusion 575. Protrusion 575, as well as protrusion 587 disposed on holding plate 580 are means of attaching indicator component 520 to durable component 600 of system 500.

Durable component 600 is shown in top perspective view in FIG. 20. Durable component 600, with proximal end 620 and distal end 630, has a housing 602 with a pair of windows, first window 604a, and second window 604b. Durable component 600 also has a flat top surface 606, conductive rings 608a and 604b, receiving element 605, protrusion 610, activation button 650, and finger grip 660.

Though not shown, a pair of spectrophotometers are disposed in housing 602. The first spectrophotometer is adjacent to and in optical communication with first window 604a, while the second spectrophotometer is adjacent to and in optical communication with second window 604b. The first spectrophotometer is in optical communication with colorimetric analyte sensing element 530a, and the second spectrophotometer is in optical communication with colorimetric analyte sensing element 530b. While the durable component 600 has been shown with two spectrophotometers, additional spectrophotometers may be included for measurements of additional analytes or bodily fluid conditions, such as pH, temperature, etc. Indicator zone 521 is the area of indicator component 520 where colorimetric analyte sensing element 530a is exposed to light source(s).

Thought not shown, durable component 600 also has a printed circuit board (PCB) with a computing system having one or more processors and a memory, as well as means for electronic communication to send the results of analyses to data processing systems that are external to system 500.

Data processing systems that may be used include at least one external device including server computers, client computers, and handheld devices such as cellphones.

As discussed in the other embodiments of this document, the spectrophotometers may include at least one or more, or two or more, or four or more, or six or more light sources and at least one, or at least two or more photodetectors. Also, as mentioned earlier, light sources in durable component 600 may be light-emitting diodes (LEDs), and more specifically, RGB LEDs. The light sources may sequentially emit red light, green light, and blue light, allowing for the near simultaneous collection of three data points, or, the sequence of emitted red light, green light, and blue light may vary.

Photodetectors in durable component 600 also, as discussed previously, may specifically measure the red, green, and blue light, allowing data to be obtained in narrow wavelength regions, and may be coated with a protective material to reduce the possibility of damage to their components.

FIG. 18 shows a top perspective view of durable component 600 and indicator component 520 assembled to form system 500. Here, indicator component 520 is disposed on distal end 630 of durable component 600. Top plate 570 of durable component 600 has protrusion 575, and holding plate 580 has protrusion 587. Durable component 600 has receiving element 605 and protrusion 610. To releasably attach indicator component 520 to durable component 500, protrusion 575 of top plate 570 is disposed in receiving element 605 of durable component 600. Then, protrusion 587 of holding plate 580 is engaged with protrusion 610 of durable component 600 with a snap connection.

FIG. 20 shows conductive strips 608a and 608b disposed on top surface 606 of durable component 600. Conductive strips 608a and 608b act as a moisture sensor in system 500. They are arranged and configured to communicate the presence of moisture in colorimetric analyte sensing elements 530a, 530b to the computing system disposed in durable component 600. In this embodiment, conductive strips 608a are associated with first window 604a and colorimetric analyte sensing element 530a. Conductive strips 308b are associated with second window 604b and colorimetric analyte sensing element 530b. The computing system disposed in durable component 600 is operatively connected to the moisture sensors as well as the components of the spectrophotometer.

The mode of operation of conductive strips 608a and 608b as moisture sensors are identical to the operation of conductive strips 108a and 108b as described in FIGS. 7 and 8. The moisture front progresses partially, and finally, fully across conductive strips 608a and 608b.

A durable component may be matched with a plurality of indicator components to create a kit for measuring analyte concentration in an absorbent article comprising. For example, the kit may have a durable component 100, 300, 600 (described above) and a plurality of indicator components, 20, 220, 520 (also described above). To ensure integrity of the indicator components during storage, each such indicator component is enclosed in an individual package.

The present invention also includes a method of measuring analyte concentration in an absorbent article. Bodily fluid is collected and transported via a transport layer to at least one colorimetric analyte sensing element. The presence of the bodily fluid at the at least one colorimetric analyte sensing element begins a countdown for a predetermined time period. Optical data relating to the colorimetric analyte sensing element is collected by at least one spectrophotometer after the predetermined time period. The optical data is communicated to a computing system having at least one processor and data storage. The optical data is analyzed to determine at least one analyte concentration in the bodily fluid.

The predetermined time period following bodily fluid contact with the colorimetric analyte sensing element could be greater than 15 seconds, or greater than 30 seconds, or greater than 60 seconds, or greater than 120 seconds, or greater than 240 seconds, or greater than 300 seconds, or greater than 360 seconds or more. The predetermined time period following bodily fluid contact with the colorimetric analyte sensing element could be a predetermined time range, for example, from about 15 to about 360 seconds, or from about 30 to about 240 seconds, or from about 120 to about 180 seconds, or from about 240 to about 360 seconds.

The analyte measured by system may be, glucose, ketone, bilirubin, blood, pH, protein, urobilinogen, nitrite, leukocytes, and/or creatinine, among others.

The analytes found in bodily fluids potentially carries evidence of developing metabolic system problems. There is a desire for people in and out of the medical establishment to track and analyze changes in the concentration of analytes in bodily fluids over time. These changes may be useful for predicting risk of a future disease conditions. Therefore, the systems discussed in the present invention allow for a method for predicting risk of a future disease condition.

As above, bodily fluid is collected and transported via a transport layer to at least one colorimetric analyte sensing element. The presence of the bodily fluid at the at least one colorimetric analyte sensing element begins a countdown for a predetermined time period. Optical data relating to the colorimetric analyte sensing element is collected by at least one spectrophotometer after the predetermined time period. The optical data is communicated to a computing system having at least one processor and data storage. The optical data is analyzed to determine at least one analyte concentration in the bodily fluid. A threshold analyte concentration of the at least one analyte concentration that indicates the risk of developing a future disease condition is compared against the at least one analyte concentration, and this can be recorded over time. Thus, the risk of developing a future disease condition may be monitored over time.

The system may be arranged, configured, and programmed with multiple photodetectors 124 and multiple colorimetric analyte sensing elements 30 to determine multiple analyte concentrations in the bodily fluid.

Non-invasively measuring the analyte concentration in bodily fluids is also ideally suited for epidemiological studies to rapidly identify problems prevalent in specific geographies or for specific populations of people. The analyte concentration measurements from system 10 may be collected over a wide population for long periods of time. The collected data may be studied to determine relationship between various analyte levels and disease states, or combined with other physiological parameter such as blood pressure, blood oxygen level, and pulse rate, or with vital statistics such as age, sex, weight, and nationality, to create a predictive model of future disease states as a function of the saved parameters. The foregoing methods may employ a system deployed in or in conjunction with an absorbent article, such as a diaper or pad, or they may employ directly contacting bodily fluids without the use of an absorbent article. For example, system 500 may be attached to a body-facing surface of the diaper. System 500 of FIGS. 18-20 may be directly contacted with bodily fluids. It may be dipped into bodily fluids that are first collected in a specimen container by grasping system 500 by finger grip 660 on proximal end 620 of durable component 600. System 500 may be energized by user engaging activation button 650 on proximal end 620 of durable component 600 before or after placing distal end 630 into specimen container. Alternatively, the indicator component of system 500 may be placed in a stream of bodily fluids such as urine as the fluid is expelled from the human body. In these uses, durable component 600 is a handheld analyzer.

EXAMPLES

Example 1: Demonstration of the Stability of Reflectance Values Versus Time in a Colorimetric Analyte Sensing Element To test the changes in reflectance values versus time, measurements of reflective values were performed with a prototype spectrophotometer on a series of prototype colorimetric analyte sensing elements which were exposed to glucose solutions at room temperature.

The prototype spectrophotometer was constructed using the following elements:
Light sources 122: RGB LEDs with light wavelengths 624, 525, and 468 nm from INOLUX (Santa Clara, Calif.). The part number is IN-S66TATRGB.
Photodetector 124: An integrated circuit (IC) color light-to-digital converters with Infrared (IR) Filter. The integrated circuit provides digital values of Red, Green, Blue (RGB), and clear light sensing. An IR blocking filter minimized the IR light spectral component which allowing color measurements to be made accurately. The part number was TCS34725, available from ams AG (Premstaetten, Austria).

The prototype colorimetric analyte sensing elements 30 were porous polysulfone membranes from PortaScience Inc. (Moorsetown, N.J.). The membranes were infused with the following mixture:
Glucose oxidase: 16.3% W/W
Horseradish peroxidase: 0.6% W/W
Potassium iodide: 7% W/W
60.7% W/W buffer, and
16.7% W/W non-reactive ingredients.

The tests were performed with artificial urine solutions with a glucose concentration of 25 milligrams/deciliter. All tests were performed at room temperature.

Light scans at three wavelengths (red, green, blue) were performed on dry colorimetric analyte sensing elements so that a baseline color of the element was established. Then, the colorimetric analyte sensing elements were saturated with the artificial urine solutions. Measurements of reflectivity were performed at three channels (red, green, and blue) of light every thirty seconds, and reflectivity was recorded.

Table 1.1 shows the reflectivity off of the saturated colorimetric analyte sensing elements at each wavelength at each time point.

TABLE 1.1

Reflectivity measurements in three light channels of colorimetric analyte sensing elements saturated in artificial urine solutions containing a 25 milligrams/deciliter glucose.

| Time (seconds) | Red | Green | Blue |
| --- | --- | --- | --- |
| 0 | 1478 | 2422 | 3882 |
| 30 | 1250 | 1885 | 3668 |

TABLE 1.1-continued

Reflectivity measurements in three light channels of colorimetric analyte sensing elements saturated in artificial urine solutions containing a 25 milligrams/deciliter glucose.

| Time (seconds) | Red | Green | Blue |
| --- | --- | --- | --- |
| 60 | 1169 | 1736 | 3600 |
| 90 | 1127 | 1663 | 3569 |
| 120 | 1096 | 1613 | 3541 |
| 150 | 1075 | 1575 | 3518 |
| 180 | 1056 | 1546 | 3499 |

The table shows reflectivity of light at each of the tested wavelengths decreased as time increased.

Next, relative variation of the traces were calculated using the following equation:

$$\text{Relative Variation } (t_2) = 100 * [\text{Reflectance } (t_1) - \text{Reflectance } (t_2)]/\text{Reflectance } (t_0),$$

where:
Reflectance ($t_1$) and Reflectance ($t_2$) are the reflectance measurements at time 1 and time 2, respectively, and
Reflectance ($t_0$) is the reflective measurement of the dry colorimetric analyte sensing element.

The units of the Relative Variation are percent (%).

For example, using the reflective measurements for the green channel from Table 1.1, the Relative Variation was at 60 seconds was calculated as:

$$\text{Relative Variation } (t_{60}) = 100 * [1885 - 1736]/2422 = 6.15\%$$

Table 1.2 shows the Relative Variation of the reflective measurements for the green channel from the colorimetric analyte sensing elements at each time point.

TABLE 1.2

Relative Variation of the green channel reflective measurements versus time.

| Time (seconds) | Relative variation - Green channel |
| --- | --- |
| 0 | Reference |
| 30 | 22.17% |
| 60 | 6.15% |
| 90 | 3.01% |
| 120 | 2.06% |
| 150 | 1.57% |
| 180 | 1.20% |

The table shows, the last three values of Relative Variation converging. So, in this example, the data taken 150 seconds after the colorimetric analyte sensing element is saturated with glucose solution may be used in the algorithm to assess the glucose concentration. Or the algorithm may use the data taken between 120 and 180 seconds after the colorimetric analyte sensing element is saturated with glucose solution in testing for glucose.

In other embodiments, the converging values of Relative Variation may be used to dictate the appropriate time to record data. So, for example, when Relative Variation falls below two percent, or one and a half percent, the algorithm may choose that point in time as the time to record the data.

Of course, the limits of this test when compared to realistic conditions include the temperature of the solution as well as the rate real urine will saturate the colorimetric analyte sensing element in the system. However, this qualitative example could be reflective of the real process. Extensive testing in realistic conditions must be continued.

Example 2: Demonstration of the Stability of Reflectance Values Versus Time in a Colorimetric Analyte Sensing Element with a Moisture Sensor As mentioned above, conductive strips 108a and 108b act as a moisture sensor in system 10 and are arranged and configured to communicate the presence of moisture in colorimetric analyte sensing element 30 to the computing system disposed in durable component 100. In this example, measurements of reflective values were performed with a prototype spectrophotometer on a series of prototype colorimetric analyte sensing elements which were exposed to glucose solutions at room temperature, where a moisture sensor was used to initiate the testing for analytes in the colorimetric sensor.

The prototype spectrophotometer and prototype colorimetric analyte sensing elements were the same as those used in Example 1, as was the artificial urine solution (glucose concentration of 25 milligrams/deciliter). As in Example 1, all tests were performed at room temperature.

The test was performed as follows:
1. 1.5 ml of the artificial urine was applied at the periphery of the prototype colorimetric analyte sensing element at the 3 o'clock position.
2. The capacitor moisture sensor showed full wetting of the sensor in less than 20 seconds.
3. The prototype colorimetric analyte sensing element was placed upside on prototype spectrophotometer and measurements of reflectivity were performed at three channels (red, green, and blue) of light every sixty seconds. The reflectivity was recorded.

Table 2.1 shows the reflectivity off of the saturated colorimetric analyte sensing elements at each wavelength at each time point.

TABLE 2.1

Reflectivity measurements in three light channels of colorimetric analyte sensing elements saturated in artificial urine solutions containing a 25 milligrams/deciliter glucose.

| Time (seconds) | Red | Green | Blue |
| --- | --- | --- | --- |
| 0 | 2382 | 3822 | 6877 |
| 60 | 2057 | 3215 | 6739 |
| 120 | 1953 | 3053 | 6658 |
| 180 | 1890 | 2957 | 6605 |
| 240 | 1863 | 2892 | 6587 |
| 300 | 1838 | 2850 | 6556 |
| 360 | 1821 | 2823 | 6530 |

The Relative Variation of the reflective measurements for the green channel were calculated as shown in Example 1. Table 2.2 shows the Relative Variation of the reflective measurements at each time point.

TABLE 2.2

Relative Variation of the green channel reflective measurements versus time.

| Time (seconds) | Relative variation - Green channel |
| --- | --- |
| 0 | Reference |
| 60 | 15.88% |
| 120 | 4.24% |
| 180 | 2.51% |
| 240 | 1.70% |
| 300 | 1.10% |
| 360 | 0.71% |

The table shows, the last three values of Relative Variation show conversion of the data. So, in this example, the data taken 240 or 300 seconds after the colorimetric analyte sensing element is saturated with glucose solution may be good to use in the algorithm to assess the glucose concentration. Or the algorithm may use the data taken between 240 and 360 seconds after the colorimetric analyte sensing element is saturated with glucose solution in testing for glucose.

The specification, embodiments, and examples above are presented to aid in the complete and non-limiting understanding of the invention disclosed herein. Since many variations and embodiments of the invention can be made without departing from its spirit and scope, the invention resides in the claims hereinafter appended.

What is claimed is:

1. A method for predicting risk of a future disease condition comprising:
   a) collecting and transporting bodily fluid to at least one colorimetric analyte sensing element,
   b) detecting the presence of bodily fluid in contact with the at least one colorimetric analyte sensing element and beginning a countdown,
   c) counting down a predetermined time period after detecting the presence of the bodily fluid in contact with the colorimetric analyte sensing element and then collecting optical data relating to the at least one colorimetric analyte sensing element with at least one spectrophotometer,
   d) communicating the optical data to a computing system having at least one processor and data storage,
   e) analyzing the optical data to determine at least one analyte concentration in the bodily fluid,
   f) identifying a threshold analyte concentration of the at least one analyte in the bodily fluid that is an indicator of the risk of developing a future disease condition; and
   g) recording the at least one analyte concentration in the bodily fluid over time.

2. The method of claim 1 wherein the bodily fluid is urine.

3. The method of claim 1 wherein the analyte is selected from the group consisting of glucose, ketones, bilirubin, blood, protein, urobilinogen, nitrite, leukocytes, and/or creatinine, and combinations thereof.

4. The method of claim 1 further comprising the step of placing a system comprising a first indicator component and a durable component into an absorbent article that is arranged and configured to perform steps a)-f) of claim 1 and recording the at least one analyte concentration in the bodily fluid.

* * * * *